US011495350B2

(12) United States Patent
Nakajima et al.

(10) Patent No.: US 11,495,350 B2
(45) Date of Patent: Nov. 8, 2022

(54) INFORMATION PROCESSING APPARATUS, INFORMATION PROCESSING METHOD, AND NON-TRANSITORY COMPUTER-READABLE STORAGE MEDIUM INFORMATION PROCESSING PROGRAM

(71) Applicants: OMRON HEALTHCARE CO., LTD., Muko (JP); OMRON CORPORATION, Kyoto (JP)

(72) Inventors: Hiroshi Nakajima, Kyoto (JP); Hirotaka Wada, Kyoto (JP); Tomohiro Kukita, Kyoto (JP); Daisuke Nozaki, Kyoto (JP); Natsuko Horiguchi, Kyoto (JP); Tamio Ueda, Takatsuki (JP)

(73) Assignees: OMRON HEALTHCARE CO., LTD., Muko (JP); OMRON CORPORATION, Kyoto (JP)

( * ) Notice: Subject to any disclaimer, the term of this patent is extended or adjusted under 35 U.S.C. 154(b) by 283 days.

(21) Appl. No.: 16/860,149

(22) Filed: Apr. 28, 2020

(65) Prior Publication Data
US 2020/0258623 A1    Aug. 13, 2020

Related U.S. Application Data

(63) Continuation of application No. PCT/JP2018/041714, filed on Nov. 9, 2018.

(30) Foreign Application Priority Data

Nov. 27, 2017 (JP) .............................. JP2017-227055

(51) Int. Cl.
*G08B 23/00* (2006.01)
*G16H 40/63* (2018.01)
(Continued)

(52) U.S. Cl.
CPC ............. *G16H 40/63* (2018.01); *A61B 5/021* (2013.01); *A61B 5/02225* (2013.01);
(Continued)

(58) Field of Classification Search
CPC ........ G16H 40/63; G16H 40/67; A61B 5/021; A61B 5/02225; A61B 5/681;
(Continued)

(56) References Cited

U.S. PATENT DOCUMENTS

2009/0264773 A1   10/2009  Kishimoto et al.
2018/0182492 A1   6/2018  Yamashita
(Continued)

FOREIGN PATENT DOCUMENTS

CN      101309636 A    11/2008
JP      2006-259827 A   9/2006
(Continued)

OTHER PUBLICATIONS

Jan. 15, 2019 Search Report issued International Patent Application No. PCT/JP2018/041714.
(Continued)

*Primary Examiner* — Toan N Pham
(74) *Attorney, Agent, or Firm* — Oliff PLC

(57) ABSTRACT

An information processing apparatus according to an aspect of the present invention includes a situation specifying unit configured to specify a part of a situation of the measurement subject on the basis of the number of measurements of the biological information in each situation of the measurement subject at the time of measuring biological information of the measurement subject by a biological information measuring unit, a current situation detecting unit configured to detect a current situation of the measurement subject, and a support information output unit configured to output support information relating to measurement of the biologi-
(Continued)

cal information if the current situation corresponds to the measurement promoting situation.

8 Claims, 8 Drawing Sheets

(51) Int. Cl.
    *A61B 5/021*     (2006.01)
    *A61B 5/022*     (2006.01)
    *A61B 5/00*     (2006.01)

(52) U.S. Cl.
    CPC ....... *A61B 5/681* (2013.01); *A61B 2560/0242* (2013.01); *A61B 2560/0252* (2013.01); *A61B 2560/0257* (2013.01); *A61B 2562/029* (2013.01); *A61B 2562/0219* (2013.01)

(58) Field of Classification Search
    CPC .... A61B 2560/0242; A61B 2560/0252; A61B 2560/0257; A61B 2562/0219; A61B 2562/029
    See application file for complete search history.

(56) References Cited

U.S. PATENT DOCUMENTS

| 2018/0256095 A1* | 9/2018 | Arnold ............... A63B 24/0062 |
| 2021/0000419 A1* | 1/2021 | Gil ..................... A61B 5/14552 |
| 2021/0166798 A1* | 6/2021 | Kukita .................. G16H 15/00 |

FOREIGN PATENT DOCUMENTS

| JP | 2006-320735 A | 11/2006 |
| JP | 2007-135818 A | 6/2007 |
| JP | 2014-168710 A | 9/2014 |
| JP | 2017-23546 A | 2/2017 |
| JP | 2017-38844 A | 2/2017 |

OTHER PUBLICATIONS

May 28, 2020 International Preliminary Report on Patentability issued in PCT/JP2018/041714.
Apr. 13, 2021 Office Action issued in Japanese Patent Application No. 2017-227055.
Aug. 17, 2022 Office Action issued in Chinese Patent Application No. 201880075973.8.

* cited by examiner

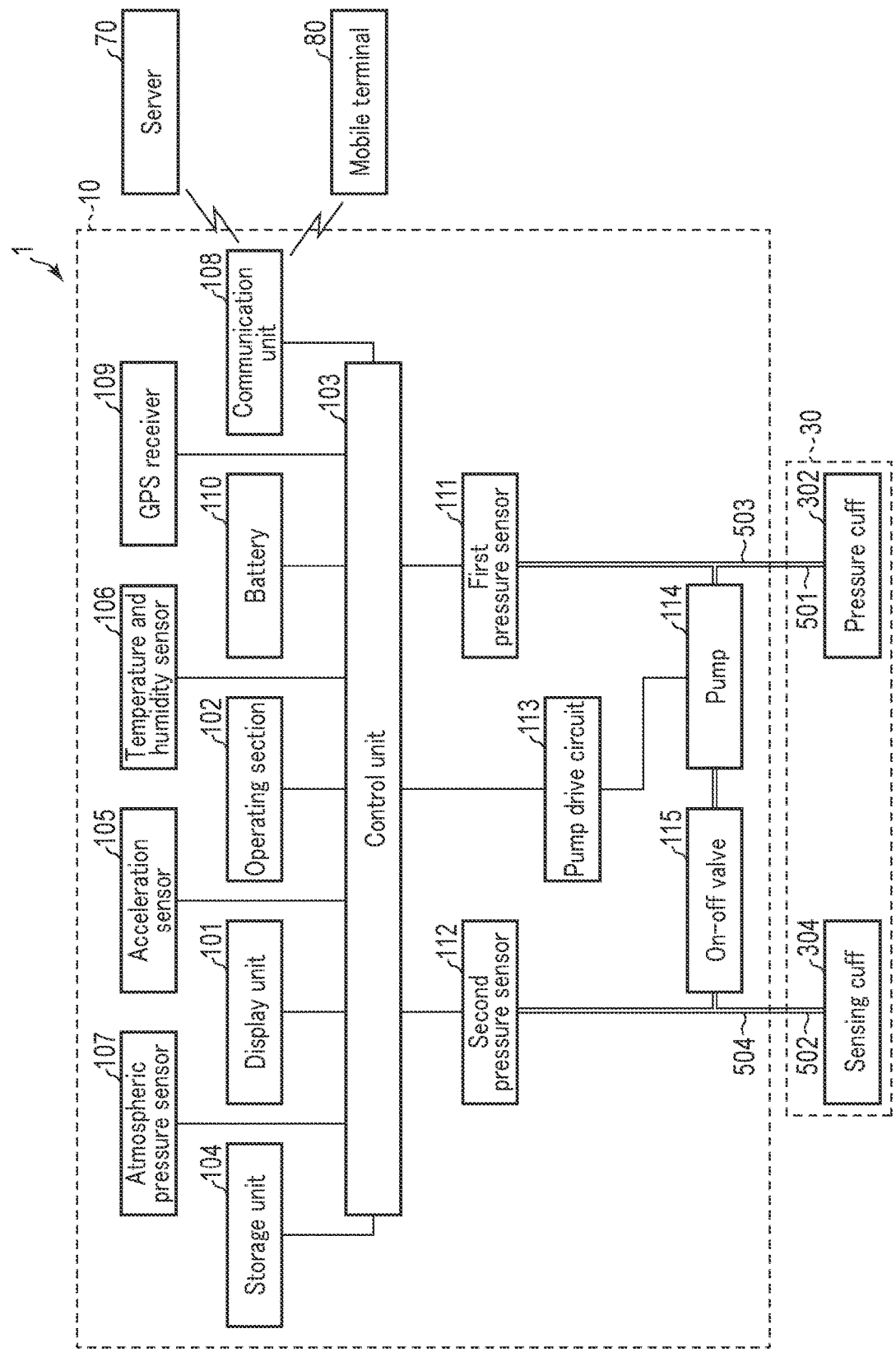
F I G. 2

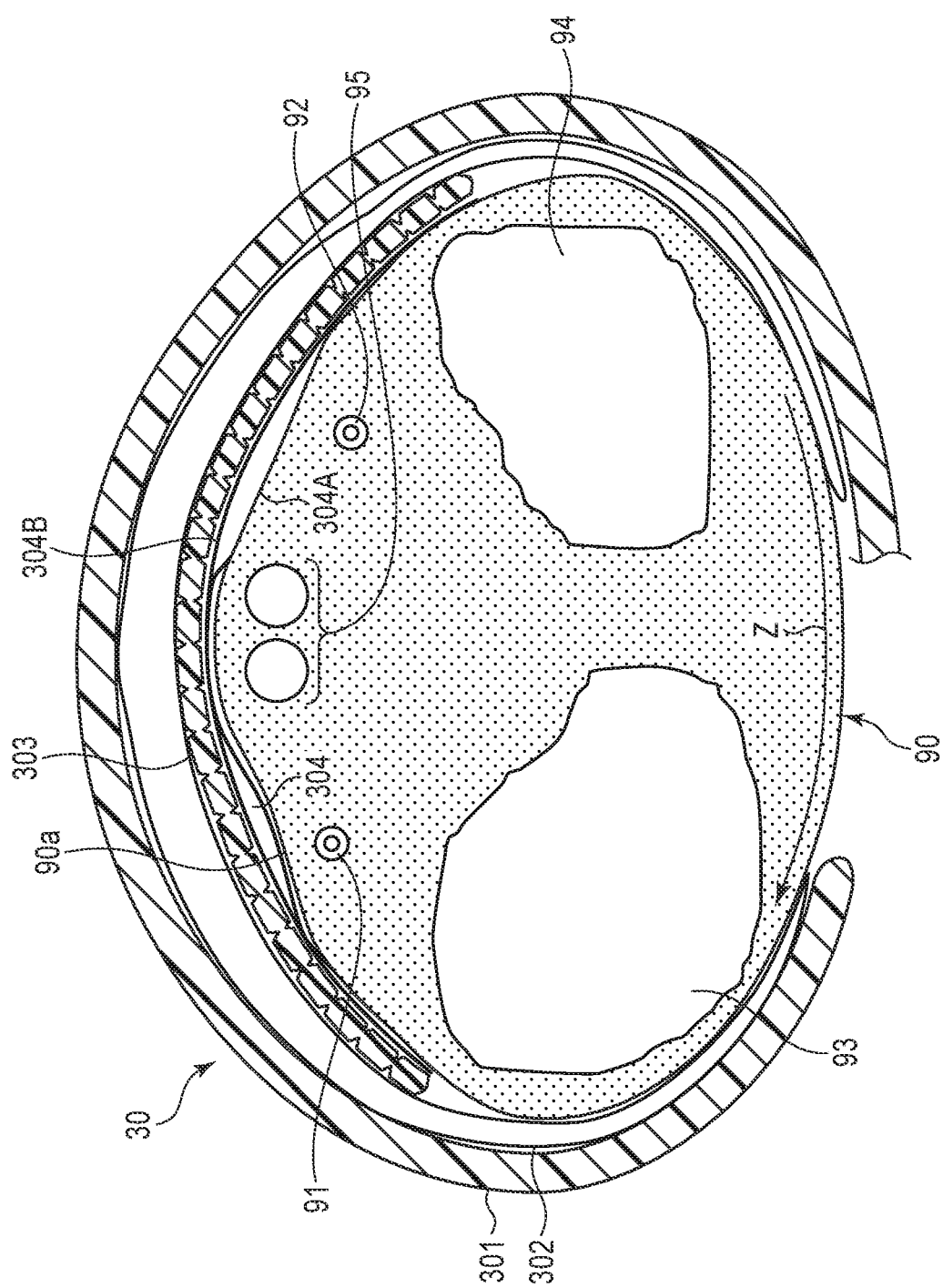
F I G. 3

| Blood pressure related information |||| 
|---|---|---|---|
| Blood pressure information | Blood pressure measurement situation |||
| | Time information | Position information | Acceleration information |
| 140/80 | 2017/05/01/07:00 | ... | ... |
| 135/82 | ... | ... | ... |
| ... | ... | ... | ... |

000# INFORMATION PROCESSING APPARATUS, INFORMATION PROCESSING METHOD, AND NON-TRANSITORY COMPUTER-READABLE STORAGE MEDIUM INFORMATION PROCESSING PROGRAM

CROSS-REFERENCE TO RELATED APPLICATIONS

This application is a Continuation Application of PCT Application No. PCT/JP2018/041714, filed Nov. 9, 2018 and based upon and claiming the benefit of priority from Japanese Patent Application No. 2017-227055, filed Nov. 27, 2017, the entire contents of all of which are incorporated herein by reference.

FIELD

The present invention relates generally to an information processing apparatus, an information processing method, and a non-transitory computer-readable storage medium.

BACKGROUND

Recent years have seen the development of wearable biological information measurement devices capable of measuring biological information, such as blood pressure, easily at any place. As an example, Jpn. Pat. Appln. KOKAI Publication No. 2017-023546 discloses a wearable blood pressure monitor that starts blood pressure measurement in response to input operation of a measurement instruction.

With such a wearable blood pressure monitor, blood pressure can be easily measured in various situations. For example, it is possible to measure and record blood pressure values at various places such as at home or a workplace, and to measure and record the blood pressure values at various times including when a user is away from home. The blood pressure values measured in such various situations are utilized for health care, etc.

SUMMARY

By using the wearable blood pressure monitor as described above, blood pressure can be measured and the measured value can be recorded in various situations such as at home or at a workplace. However, an insufficiency, deviation, or variation (hereinafter also referred to as "insufficiency, etc.") may occur in the number of measured blood pressure values in respective situations due to a failure to measure. For example, among the numbers of measured blood pressure values in respective situations, the number of blood pressure values measured at the workplace may be smaller than the number of blood pressure values measured at home. If the insufficiency, etc. occurs in the number of measured blood pressure values in each situation, health management based on blood pressure values in each situation may be insufficient.

In one aspect, the present invention is made in light of such an actual situation, and the object of the present invention is to provide a technique for supporting the resolution of an insufficiency, etc. in the number of pieces of measured biological information in each situation of a measurement subject.

In order to solve the above problem, the present invention employs the following configuration.

That is, an information processing apparatus according to a first aspect of the present invention includes a situation specifying unit configured to specify a part of a situation of the measurement subject on the basis of the number of measurements of the biological information in each situation of the measurement subject at the time of measuring biological information of the measurement subject by a biological information measuring unit, a current situation detecting unit configured to detect a current situation of the measurement subject, and a support information output unit configured to output support information relating to measurement of the biological information if the current situation corresponds to the measurement promoting situation.

According to the above-described configuration, the support information relating to the measurement of the biological information is output if the current situation corresponds to the measurement promoting situation, which leads to an expectation that the biological information will be measured and recorded in the measurement promotion situation. As a result, it is expected that an insufficiency, etc. in the number of measurements of biological information in each situation can be resolved.

According to a second aspect of the present invention, in the information processing apparatus of the first aspect, the support information is an instruction for the biological information measuring unit to measure the biological information.

According to the above configuration, the blood pressure is measured in the measurement promoting situation on the basis of the support information. As a result, it is expected that the insufficiency, etc. in the number of measurements of biological information in each situation can be resolved.

According to a third aspect of the present invention, in the information processing apparatus of the first aspect, the support information is information for prompting an input operation for generating an instruction for the biological information to measure the biological information measuring unit.

According to the above configuration, the input operation for generating the instruction to measure the biological information in the measurement promoting situation is prompted by the output of the support information, and measurement of the biological information is expected. As a result, it is expected that the insufficiency, etc. in the number of measurements of biological information in each situation can be resolved.

According to a fourth aspect of the present invention, in the information processing apparatus according to any one of the first to third aspects, the situation specifying unit generates information indicating the number of pieces of the measured biological information in each situation of the measurement subject on the basis of the situation of the measurement subject associated with each piece of biological information.

According to the above configuration, information indicating the number of measurements of the biological information in each situation is generated on the basis of the situation of the measurement subject associated with each biological information, and the measurement promoting situation can be specified on the basis of the number of measurements of biological information in each situation. For example, it is possible to specify, as a measurement promoting situation, a situation where an insufficiency, etc. in the biological information in each situation occurs, and it is expected that the insufficiency, etc. in the biological information in each situation can be resolved.

According to a fifth aspect of the present invention, in the information processing apparatus according to any one of the first to fourth aspects, the situation specifying unit specifies, as the measurement promoting situation, the part of the situation of the measurement subject in which the number of measurements of biological information is less than a specified number.

According to the above configuration, in a situation where a number of the measured biological information in each situation is less than the specified number, the measurement of the biological information can be supported, and it is expected that an insufficiency, etc. in the biological information in a situation where the number of measurements is less than the specified number can be resolved.

According to a sixth aspect of the present invention, in the information processing apparatus according to any one of the first to fourth aspects, the situation specifying unit specifies, as the measurement promoting situation, a part of the situation of the measurement subject where the number of pieces of the measured biological information is relatively small.

According to the above configuration, in a situation where a number of measurements of biological information for each situation is relatively small, the measurement of the biological information can be supported, and it is expected that an insufficiency, etc. in the biological information in a situation where the number of measurements is relatively small can be resolved.

According to a seventh aspect of the present invention, in the information processing apparatus according to any one of the first to sixth aspects, the current situation detecting unit detects at least one of time information, position information, acceleration information, temperature and humidity information, atmospheric pressure information, or action schedule information, as the current situation of the measurement subject.

According to the above configuration, it is possible to detect the current situation according to at least one of time information, position information, acceleration information, temperature and humidity information, atmospheric pressure information, or action schedule information.

An information processing method according to an eighth aspect of the present invention is an information processing method performed by an information processing apparatus that supports the operation of a biological information measuring unit, and includes a situation specifying process to specify a part of the situation of a measurement subject as a measurement promoting situation on the basis of a number of measurements of biological information in each situation of the measurement subject when the biological information measuring unit measures the biological information of the measurement subject, a current situation detecting process to detect the current situation of the measurement subject, and a support information outputting process to output support information relating to the measurement of the biological information if the current situation corresponds to the measurement promoting situation.

According to the above-described configuration, an effect similar to that in the first aspect can be obtained.

A ninth aspect of the present invention is a non-transitory computer-readable storage medium storing an information processing program for causing a computer to function as each unit included in the information processing apparatus according to any one of the first to seventh aspects.

According to the above-described configuration, the information processing program can obtain an effect similar to that in any one of the above-described first to seventh aspects.

According to the present invention, it is possible to provide a technique for supporting the resolution of an insufficiency, etc. in the number of the measurements of biological information in each situation of the measurement subject.

BRIEF DESCRIPTION OF THE DRAWINGS

FIG. 2 is a block diagram showing an example of a blood pressure monitor according to an embodiment.

FIG. 3 is a cross-sectional view showing an example of a blood pressure monitor according to an embodiment.

DETAILED DESCRIPTION

An embodiment according to one aspect of the present invention (hereinafter also referred to as "the present embodiment") will be described with reference to the drawings. However, the present embodiments described below are merely illustrative of the present invention in all respects. It is needless to say that various improvements and modifications can be made without departing from the scope of the present invention. That is, a specific configuration according to the embodiment may be appropriately adopted when implementing the present invention. Although signals appearing in the present embodiments are described in natural language, more concretely, signals are designated by pseudo language, commands, parameters, machine language, etc. that are recognizable by a computer.

First Embodiment (Configuration)

Figure 1:
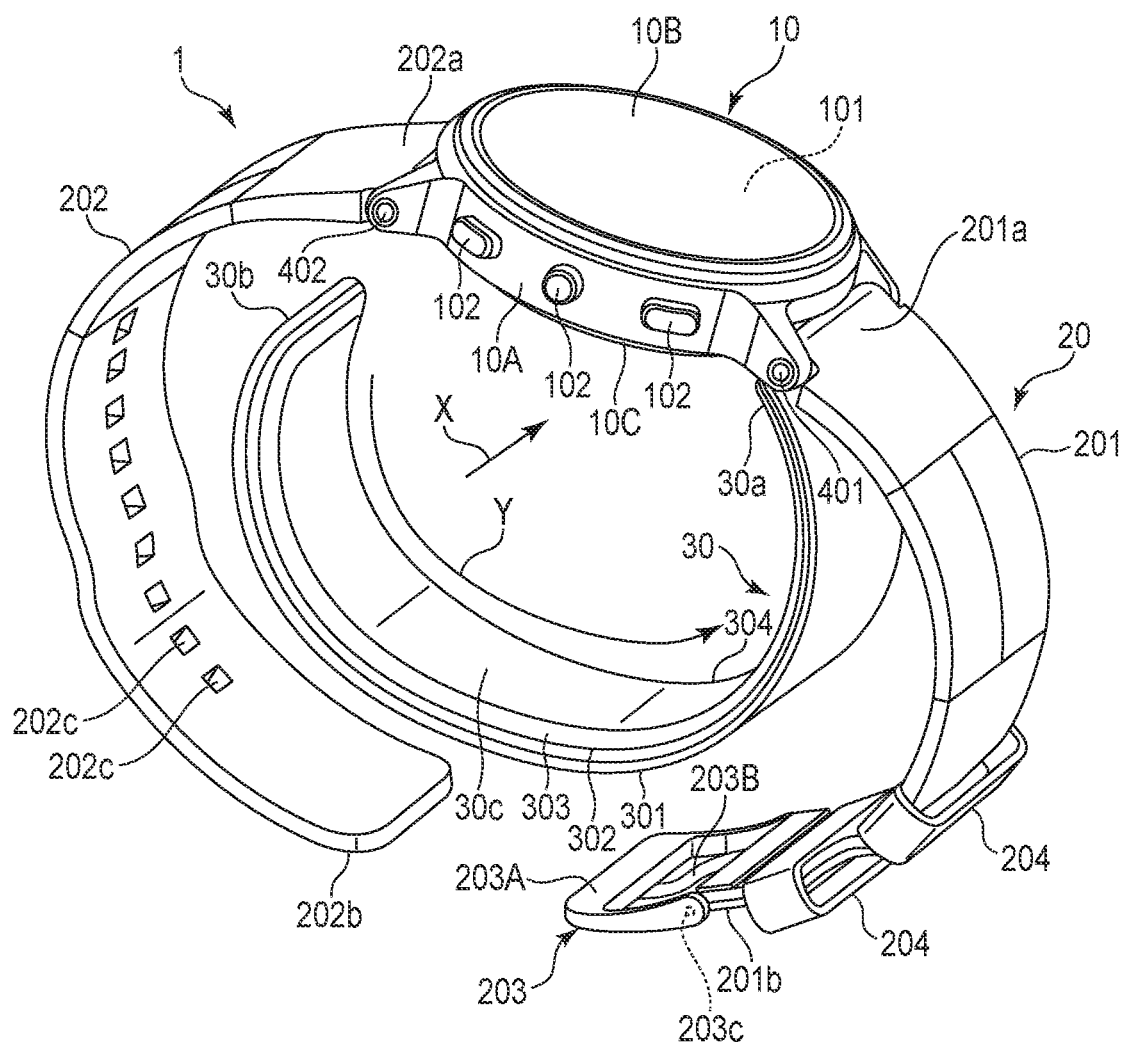
FIG. 1 is an external view showing an example of a blood pressure monitor according to an embodiment.

FIG. 1 is a diagram showing an external appearance of a blood pressure monitor 1 according to an embodiment of an information processing apparatus according to the present invention.

The blood pressure monitor 1 is a wristwatch-type wearable device. The blood pressure monitor 1 has a blood pressure measuring function as a blood pressure measuring unit, and further has various information processing functions. The information processing functions include, for example, an activity amount measuring function, a footstep counting function, a sleeping state measuring function, and an environment (temperature and humidity) measuring function. The blood pressure monitor 1 is, for example, a blood pressure monitor of a type in which blood pressure measurement is started on the basis of an input of an instruction to start blood pressure measurement from the measurement subject, or on a trigger signal autonomously generated by the blood pressure monitor 1.

The blood pressure monitor 1 includes a main body 10, a belt 20, and a cuff structure 30.

A configuration of the main body 10 will be explained below.

The main body 10 is configured to be equipped with a plurality of elements such as a control system of the blood pressure monitor 1.

The main body 10 includes a case 10A, a glass 10B, and a back cover 10C.

The case 10A is in an approximate short cylindrical shape, for example. The case 10A has a pair of projected lugs for attaching the belt 20 to two respective parts on the side surface of the case 10A.

The glass 10B is attached to the upper part of the case 10A. The glass 10B is in a circular shape, for example.

The back cover 10C is detachably attached to the lower part of the case 10A, in order to face the glass 10B.

The main body 10 is equipped with a display unit 101 and an operating section 102.

The display unit 101 displays various types of information. The display unit 101 is inside the main body 10, and is provided at a position where a measurement subject can visually recognize the display unit 101 through the glass 10B. The display unit 101 is, for example, a liquid crystal display (LCD). The display unit 101 may be an organic electro luminescence (EL) display. The display unit 101 only has to have a function to display various information, and is not limited to the above. The display unit 101 may include a light emitting diode (LED).

The operating section 102 is an element for inputting various instructions for the blood pressure monitor 1. The operating section 102 is provided on the side surface of the main body 10. The operating section 102 includes, for example, one or more push-type switches. The operating section 102 may be a pressure sensitive (resistive) or proximity (capacitance) touch panel-type switch. The operating section 102 only has to have a function to input various instructions for the blood pressure monitor 1, and is not limited to the above.

An example of a switch included in the operating section 102 will be described.

The operating section 102 includes a measurement switch for instructing starting or stopping of blood pressure measurement. Furthermore, the operating section 102 may include a home switch for returning the display screen of the display unit 101 to a predetermined home screen, and a record call switch for displaying measurement records of the past blood pressure, the activity amount, etc. on the display unit 101.

The main body 10 includes a plurality of elements other than the display unit 101 and the operating section 102. A plurality of elements equipped in the main body 10 will be described later.

The configuration of the belt 20 will be described.

The belt 20 is configured to encircle a portion to be measured (e.g. the left wrist) of a measurement subject. The width direction of the belt 20 is set to an X direction. The direction in which the belt 20 encircles the portion to be measured is set to a Y direction.

The belt 20 includes a first belt portion 201, a second belt portion 202, a buckle 203, and a belt holding portion 204.

The first belt portion 201 is in a band-like shape extending from the main body 10 toward one side in one direction (the right side in FIG. 1). A proximal portion 201a, which is a portion of the first belt portion 201 close to the main body 10, is attached to move rotatively with respect to the pair of lugs of the main body 10 via a connecting rod 401.

The second belt portion 202 is in a band-like shape extending from the main body 10 toward the other side in one direction (the left side in FIG. 1). A proximal portion 202a, which is a portion of the second belt portion 202 close to the main body 10, is attached to move rotatively with respect to the pair of lugs of the main body 10 via a connecting rod 402. Between the proximal portion 202a and a distal portion 202b (which is further from the main body 10) of the second belt portion 202, a plurality of small holes 202c are formed in a penetrating manner in a thickness direction of the second belt portion 202.

The buckle 203 is configured to fasten the first belt portion 201 and the second belt portion 202. The buckle 203 is attached to a distal portion 201b of the first belt portion 201 that is distant from the main body 10. The buckle 203 includes a frame-like body 203A, a tongue 203B, and a connecting rod 203C.

The frame-like body 203A and the tongue 203B are attached to move rotatively with respect to the distal portion 201b of the first belt portion 201 via the connecting rod 203C. The frame-like body 203A and the tongue 203B are made of a metal material. The frame-like body 203A and the tongue 203B may be made of a plastic material. When the first belt portion 201 is fastened to the second belt portion 202, the distal portion 202b of the second belt portion 202 is passed through the frame-like body 203A. The tongue 203B is inserted into any one of the small holes 202c of the second belt portion 202.

The belt holding portion 204 is attached between the proximal portion 201a and the distal portion 201b of the first belt portion 201. When the first belt portion 201 is fastened to the second belt portion 202, the distal portion 202b of the second belt portion 202 is passed through the belt holding portion 204.

The configuration of the cuff structure 30 will be described.

The cuff structure 30 is configured to be capable of compressing the portion to be measured upon measuring a blood pressure.

The cuff structure 30 is in a band-like shape extending along the Y direction. The cuff structure 30 faces the inner periphery of the belt 20. One end 30a of the cuff structure 30 is attached to the main body 10. The other end 30b of the cuff structure 30 is a free end. Therefore, the cuff structure 30 is separable from the inner periphery of the belt 20.

The cuff structure 30 includes a curler 301, a pressure cuff 302, a back plate 303, and a sensing cuff 304.

The curler 301 is arranged on the outermost periphery of the cuff structure 30. In the natural state, the curler 301 is curved along the Y direction. The curler 301 is a resin plate having a predetermined flexibility and hardness. The resin plate is made of, for example, polypropylene.

The pressure cuff 302 is arranged along the inner periphery of the curler 301. The pressure cuff 302 is in a bag-like shape. A flexible tube 501 (shown in FIG. 2) is attached to the pressure cuff 302. The flexible tube 501 is an element for supplying a fluid for transmitting pressure (hereinafter, simply referred to as "fluid") from the side of the main body 10, or for discharging the fluid from the pressure cuff 302. The fluid is, for example, air. When the fluid is supplied to the pressure cuff 302, the pressure cuff 302 expands and compresses the portion to be measured.

The pressure cuff 302 may include, for example, two fluid bags stacked in the thickness direction. Each fluid bag is made of, for example, a stretchable polyurethane sheet. If a fluid is supplied to the pressure cuff 302, the fluid flows into the fluid bags. Expansion of the fluid bags leads to expansion of the pressure cuff 302.

The back plate 303 is arranged along the inner periphery of the pressure cuff 302. The back plate 303 is in a band-like shape. The back plate 303 is made of, for example, resin. The resin is, for example, polypropylene. The back plate 303 functions as a reinforcing plate. Therefore, the back plate 303 can transmit the compressing force from the pressure cuff 302 to the whole area of the sensing cuff 304.

On the inner periphery and the outer periphery of the back plate 303, a plurality of grooves each having a V-shaped or U-shaped cross section and extending in the direction X are provided in parallel and separately from each other with respect to the direction Y. Since the back plate 303 is easily bent, the back plate 303 cannot prevent the cuff structure 30 from being bent.

The sensing cuff 304 is arranged along the inner periphery of the back plate 303. The sensing cuff 304 is in a bag-like shape. The sensing cuff 304 includes a first sheet 304A (shown in FIG. 3) and a second sheet 304B (shown in FIG. 3) facing the first sheet 304A. The first sheet 304A corresponds to the inner periphery 30c of the cuff structure 30. Thus, the first sheet 304A is in contact with the portion to be measured. The second sheet 304B faces the inner periphery of the back plate 303. The first sheet 304A and the second sheet 304B are, for example, stretchable polyurethane sheets. A flexible tube 502 (shown in FIG. 2) is attached to the sensing cuff 304. The flexible tube 502 is an element for supplying a fluid to the sensing cuff 304, or discharging the fluid from the sensing cuff 304.

Next, a plurality of elements mounted on the main body 10 will be described.

FIG. 2 is a block diagram showing a hardware configuration of the blood pressure monitor 1.

The main body 10 is equipped with a control unit 103, a storage unit 104, an acceleration sensor 105, a temperature and humidity sensor 106, an atmospheric pressure sensor 107, a communication unit 108, a global positioning system (GPS) receiver 109, a battery 110, a first pressure sensor 111, a second pressure sensor 112, a pump drive circuit 113, a pump 114, and an on-off valve 115, in addition to the display unit 101 and the operating section 102 described above.

The control unit 103 includes a processor, a random access memory (RAM), a read only memory (ROM), etc. constituting the computer, and controls each component in accordance with information processing on the basis of a program (information processing program) stored in at least one of the ROM or the storage unit 104 as a non-transitory computer-readable storage medium. For example, the processor is a central processing unit (CPU). The program is an instruction for operating the control unit 103.

The control unit 103 stores data acquired from the acceleration sensor 105, the temperature and humidity sensor 106, the atmospheric pressure sensor 107, the communication unit 108, the GPS receiver 109, the first pressure sensor 111, and the second pressure sensor 112, in the storage unit 104. The configuration of each unit mounted on the control unit 103 will be described later.

The storage unit 104 is, for example, an auxiliary storage device such as a hard disk drive or a solid state drive. For example, the storage unit 104 stores a program to be executed by the control unit 103. The storage unit 104 stores control data used for controlling the blood pressure monitor 1, and setting data used for setting various functions of the blood pressure monitor 1, for example. The storage unit 104 is used as, for example, a work memory when the program is executed.

The storage unit 104 stores blood pressure-related information. For example, the blood pressure-related information includes a plurality of pieces of blood pressure information measured at different dates and times, and the situation of the measurement subject at the time when the blood pressure associated with each piece of blood pressure information is measured (hereinafter also referred to as "blood pressure measurement situation"). For example, the blood pressure information includes blood pressure values (such as systolic blood pressure (SBP) and diastolic blood pressure (DBP)). Further, the blood pressure measurement situation includes at least one of time information (measurement time), position information (measurement position), acceleration information, temperature and humidity information, atmospheric pressure information, action schedule information, etc. acquired in accordance with the timing of blood pressure measurement. The blood pressure measurement situation may include at least time information. For example, the above-described timing of blood pressure measurement is any one of the timing at the start of blood pressure measurement, the timing in the middle of blood pressure measurement, and the timing at the end of blood pressure measurement. Further, the acceleration information may be information acquired in accordance with the timing of a predetermined time (for example, one minute or five minutes) before the start of blood pressure measurement.

The acceleration sensor 105 is a three-axis acceleration sensor. The acceleration sensor 105 outputs, to the control unit 103, acceleration information representing acceleration in thee directions orthogonal to each other. The acceleration information is an example of information representing the movement of the measurement subject. By using the acceleration information, the control unit 103 can calculate an activity amount not only in walking of the measurement subject but also in various activities such as household chores and desk work of the measurement subject. The activity amount is an indicator related to the activity of the measurement subject such as a moving (walking) distance, consumed calories, or a fat combustion amount. By using the acceleration information, the control unit 103 can also estimate whether the measurement subject is before sleeping, asleep, or after waking up. By using the acceleration information, the control unit 103 can also estimate whether or not the measurement subject is exercising.

The temperature and humidity sensor 106 measures environmental temperature and humidity around the blood pressure monitor 1. The temperature and humidity sensor 106 outputs environmental data representing environmental temperature and humidity to the control unit 103. For example, a temperature (change in temperature) can be considered as to be one of the factors that may cause blood pressure fluctuation in human beings. Thus, the environmental data is information that can be a factor in blood pressure fluctuation of the measurement subject.

The atmospheric pressure sensor 107 detects an atmospheric pressure. The atmospheric pressure sensor 107 outputs atmospheric pressure information to the control unit 103. By using the atmospheric pressure information and the acceleration information, the control unit 103 can measure the number of steps, the number of fast-walking steps, the number of steps up the stairs, etc. of the measurement subject.

The communication unit 108 is an interface for connecting the blood pressure monitor 1 with at least one of the server 70 or the mobile terminal 80. The mobile terminal 80 is a smartphone or a tablet terminal, for example. It is assumed that the mobile terminal 80 is owned by the measurement subject. The communication unit 108 is controlled by the control unit 103. The communication unit 108 transmits information to at least one of the server 70 or the mobile terminal 80 via a network. The communication unit 108 transfers, to the control unit 103, the information received from at least one of the server 70 or the mobile terminal 80 via the network. This communication via the network may be either wireless or wired. The network may be the Internet, but is not limited thereto. The network may be another type of network, such as a local area network (LAN) in a hospital, or may be a 1 to 1 communication using, for example, a USB cable. The communication unit 108 may include a micro USB connector. The communication unit 108 may transmit information to the mobile terminal 80 through short-range wireless communication such as Bluetooth (registered trademark).

The GPS receiver 109 receives GPS signals transmitted from a plurality of GPS satellites, and outputs the received GPS signals to the control unit 103. The control unit 103 calculates the current position of the blood pressure monitor 1, in other words, the current position of the measurement subject wearing the blood pressure monitor 1, by performing the distance measurement calculation on the basis of the above-described GPS signals. The blood pressure monitor 1 does not necessarily have a distance measurement calculation function by the GPS receiver 109 and the control unit 103. In this case, the blood pressure monitor 1 acquires position information indicating the current position calculated by the mobile terminal 80 from the mobile terminal 80 via the communication unit 108. The position information calculated by the mobile terminal 80 corresponds to the current position of the blood pressure monitor 1. For example, the mobile terminal 80 may include a GPS receiving function and calculate position information from GPS signals received by the GPS receiving function, or the mobile terminal 80 may acquire position information by communication with a base station.

The battery 110 is a rechargeable second battery, for example. The battery 110 supplies power to each element mounted on the main body 10. For example, the battery 110 supplies power to the display unit 101, the operating section 102, the control unit 103, the storage unit 104, the acceleration sensor 105, the temperature and humidity sensor 106, the atmospheric pressure sensor 107, the communication unit 108, the first pressure sensor 111, the second pressure sensor 112, the pump drive circuit 113, the pump 114, and the on-off valve 115.

The first pressure sensor 111 is, for example, a piezoresistive pressure sensor. The first pressure sensor 111 detects the pressure in the pressure cuff 302 via the flexible tube 501 and a first channel forming member 503 constituting the first channel. The first pressure sensor 111 outputs pressure data to the control unit 103.

The second pressure sensor 112 is, for example, a piezoresistive pressure sensor. The second pressure sensor 112 detects the pressure in the sensing cuff 304 via the flexible tube 502 and the second channel forming member 504 constituting the second channel. The second pressure sensor 112 outputs pressure data to the control unit 103.

The pump drive circuit 113 drives the pump 114 on the basis of control signals from the control unit 103.

The pump 114 is a piezoelectric pump, for example. The pump 114 is connected to the pressure cuff 302 via the first channel in a manner such that a fluid can circulate. The pump 114 may supply a fluid to the pressure cuff 302 via the first channel. The pump 114 is equipped with an exhaust valve (not shown) which is controlled to open or close in accordance with an on/off of the pump 114. That is, when the pump 114 is turned on, the exhaust valve closes so as to help encapsulation of the air in the pressure cuff 302. On the other hand, when the pump 114 is turned off, the exhaust valve opens so as to discharge the air inside the pressure cuff 302 to the atmosphere through the first channel. The exhaust valve functions as a check valve, and the discharged air does not flow backward.

The pump 114 is further connected to the sensing cuff 304 via the second channel in a manner such that a fluid can circulate. The pump 114 may supply a fluid to the sensing cuff 304 via the second channel.

The on-off valve 115 is inserted into the second channel forming member 504. The on-off valve 115 is a constantly open electromagnetic valve, for example. The opening and closing (degree of opening) of the on-off valve 115 is controlled on the basis of control signals from the control unit 103. When the on-off valve 115 is in the open state, the pump 114 can supply a fluid to the sensing cuff 304 via the second channel.

Next, a state where the blood pressure monitor 1 is worn on a portion to be measured (hereinafter also referred to as "wearing state") will be described.

FIG. 3 is a diagram showing a cross section perpendicular to the left wrist 90 which is a portion to be measured in the wearing state. The main body 10 and the belt 20 are not shown. FIG. 3 shows a radial artery 91, an ulnar artery 92, a radius 93, an ulna 94, and a tendon 95 of the left wrist 90.

In the wearing state, the curler 301 extends along the outer periphery (in the Z direction) of the left wrist 90. The pressure cuff 302 extends along the Z direction on the inner peripheral side of the curler 301. The back plate 303 is interposed between the pressure cuff 302 and the sensing cuff 304, and extends along the Z direction. The sensing cuff 304 comes into contact with the left wrist 90, and extends in the Z direction across an artery-passing portion 90a of the left wrist 90. The belt 20, the curler 301, the pressure cuff 302, and the back plate 303 act as compressing members capable of generating a compressing force toward the left wrist 90, and compress the left wrist 90 via the sensing cuff 304.

Next, the configuration of the software provided in the control unit 103 will be described.

Figure 4:
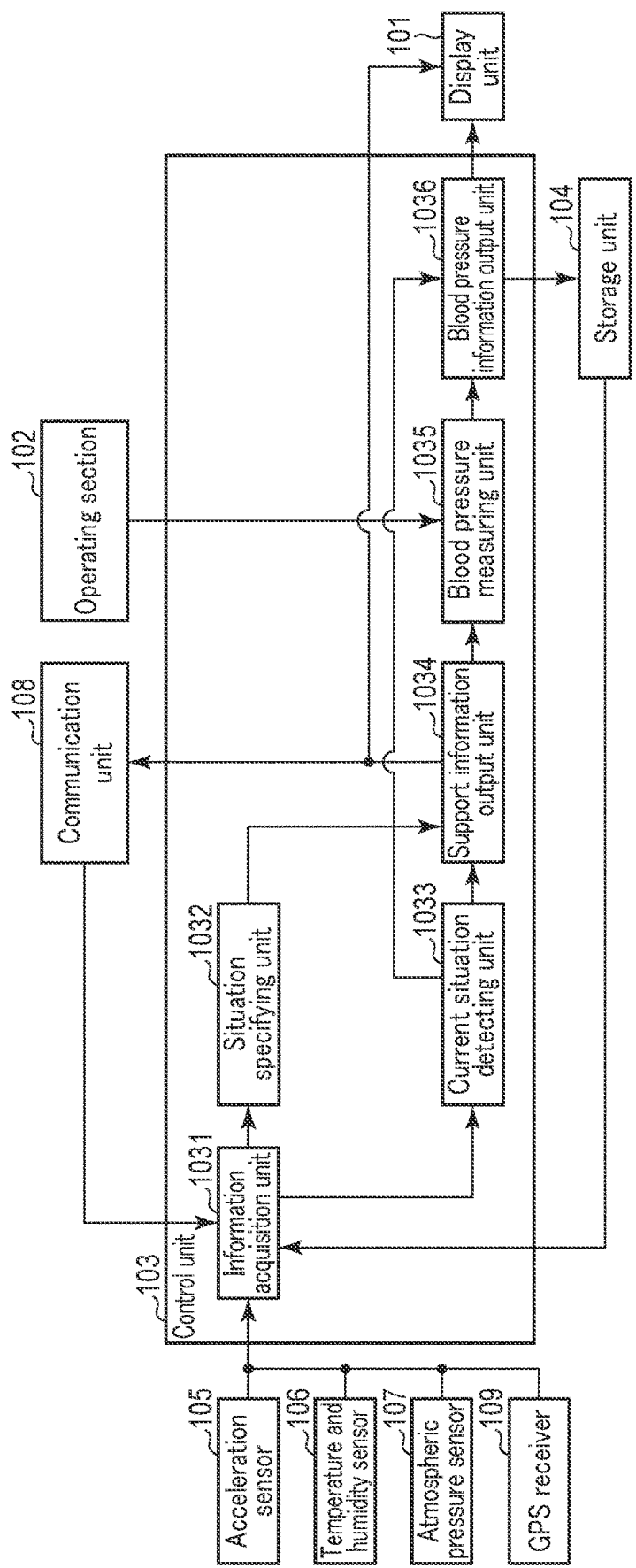
FIG. 4 is a functional block diagram showing an example of a blood pressure monitor according to an embodiment.

FIG. 4 is a block diagram showing a configuration of software included in the control unit 103 of the blood pressure monitor 1. The control unit 103 includes an information acquisition unit 1031, a situation specifying unit 1032, a current situation detecting unit 1033, a support information output unit 1034, a blood pressure measuring unit 1035, and a blood pressure information output unit 1036, as characteristic control functions according to the embodiment. All of these control functions are implemented by causing a processor to execute a program stored in a ROM, etc. Each of the control function units may be distributed and mounted on two or more processors.

The configuration of the information acquisition unit 1031 will be described.

The information acquisition unit 1031 acquires the blood pressure-related information from the storage unit 104, and outputs the blood pressure-related information to the situation specifying unit 1032. The information acquisition unit 1031 acquires at least one piece of information of the current time information, the current position information, the current acceleration information, the current temperature and humidity information, the current atmospheric pressure information, or the registered action schedule information, and outputs the at least one piece of information to the current situation detecting unit 1033. The information acquisition unit 1031 may acquire at least time information and output the time information to the current situation detecting unit 1033.

For example, the information acquisition unit 1031 acquires time information from the communication unit 108. The communication unit 108 receives time information from the server 70 or the mobile terminal 80. If the blood pressure monitor 1 has a clock function, the information acquisition unit 1031 may acquire time information provided by the clock function. In this case, the time function may correct the current date and time on the basis of the time information acquired from the communication unit 108, and provide the corrected time information.

For example, the information acquisition unit 1031 acquires a GPS signal from the GPS receiver 109. Alternatively, the information acquisition unit 1031 may acquire position information indicating the current position from the communication unit 108. For example, the information acquisition unit 1031 acquires action schedule information from the communication unit 108. The communication unit 108 receives action schedule information from the mobile terminal 80.

For example, schedule management application software is installed in the mobile terminal 80, and the schedule management application software creates and registers the action schedule information and outputs the action schedule information to the exterior. For example, the action schedule information includes a bedtime and a waking time. For example, the information acquisition unit 1031 acquires the acceleration information from the acceleration sensor 105, acquires the temperature and humidity information from the temperature and humidity sensor 106, and acquires the atmospheric pressure information from the atmospheric pressure sensor 107.

The configuration of the situation specifying unit 1032 will be described.

The situation specifying unit 1032 acquires information indicating the situation of a measurement subject at the time of measuring blood pressure information, and detects the number or frequency of measurements of blood pressure information for each blood pressure measurement situation on the basis of the acquired information indicating the situation of the measurement subject. Then, the situation specifying unit 1032 specifies a part of the situation of the measurement subject as a situation in which the measurement of the blood pressure information should be promoted (hereinafter also referred to as "measurement promoting situation") on the basis of the number or frequency of measurement of the blood pressure information for each blood pressure measurement situation, and outputs information indicating the measurement promoting situation to the support information output unit 1034.

For example, the situation specifying unit 1032 groups pieces of the blood pressure information on the basis of the blood pressure measurement situation associated with each piece of the blood pressure information. The situation specifying unit 1032 groups the pieces of the blood pressure information on the basis of at least one of the time information, position information, acceleration information, temperature and humidity information, atmospheric pressure information, and action schedule information.

For example, the situation specifying unit 1032 groups the pieces of the blood pressure information according to the time zone on the basis of the time information. Furthermore, the situation specifying unit 1032 may group the pieces of the blood pressure information into blood pressure information during sleep or blood pressure information while awake on the basis of a period of time. For example, the situation specifying unit 1032 may specify that the blood pressure information at 7:00 to 22:59 is information while awake and that the blood pressure information at 23:00 to 6:59 is information during sleep, and may group the pieces of the blood pressure information. Alternatively, the situation specifying unit 1032 may further limit a period of time so as to specify the blood pressure information at 9:00 to 20:00 as information while awake and the blood pressure information at 1:00 to 4:00 as information during sleep for grouping. Alternatively, the situation specifying unit 1032 may specify whether or not the situation is during sleep on the basis of the acceleration information so as to group the pieces of the blood pressure information according to whether or not the situation is during sleep. The situation specifying unit 1032 specifies whether or not the current position corresponds to the registered position on the basis of the position information, so as to group the pieces of the blood pressure information according to the registered position. The situation specifying unit 1032 specifies whether or not the measurement subject is exercising on the basis of the acceleration information, and groups the pieces of the blood pressure information according to the situation of whether or not the measurement subject is exercising.

Furthermore, the situation specifying unit 1032 may combine a plurality of situations to group the pieces of the blood pressure information. For example, the situation specifying unit 1032 combines the position information and the acceleration information to specify whether or not the measurement subject is moving for commuting, so as to group the pieces of the blood pressure information according to the situation of whether or not the measurement subject is moving for commuting. Further, the situation specifying unit 1032 combines the time information and the action schedule information to specify before sleep, during sleep, and after waking up, and groups the pieces of the blood pressure information according to the situation before sleep, during sleep, and after waking up. For example, "before sleep" is set to the time less than two hours before sleep, and "after waking up" is set to the time within two hours after waking up.

Figures 5, 6:
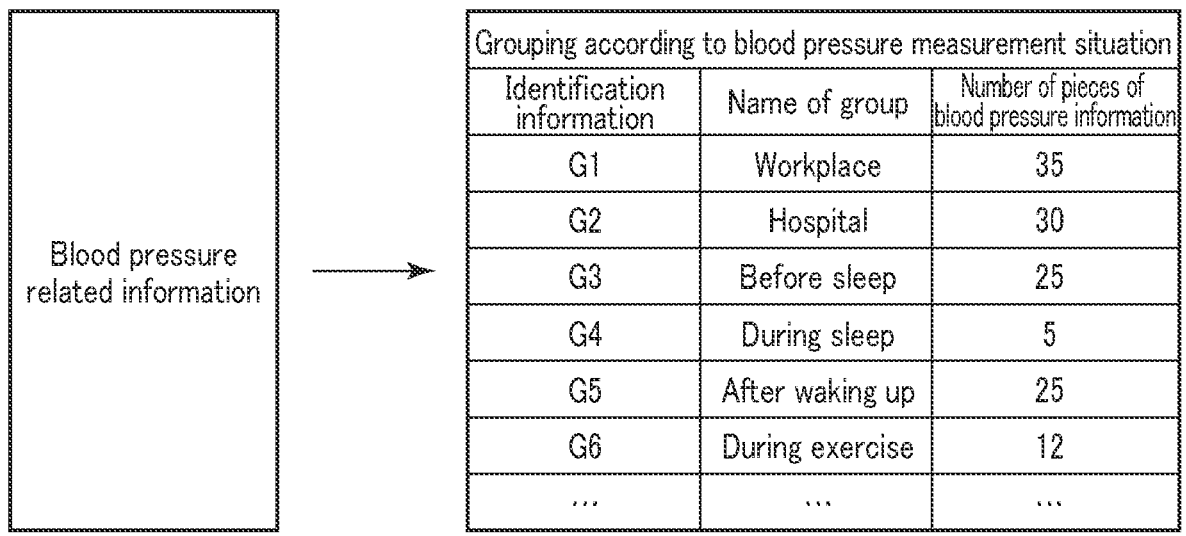
FIG. 5 is a diagram showing an example of blood pressure-related information according to an embodiment.
FIG. 6 is a diagram showing an example of grouping according to blood pressure measurement situations according to an embodiment.

FIG. 5 is a diagram showing an example of blood pressure-related information. The blood pressure-related information shown in FIG. 5 includes a plurality of pieces of blood pressure information obtained by measurements performed a plurality of times, and the blood pressure measurement situation (for example, including time information, position information, and acceleration information) associated with each piece of blood pressure information.

FIG. 6 is a diagram showing an example of grouping according to a blood pressure measurement situation. As shown in FIG. 6, for example, the situation specifying unit 1032 calculates the number of measurements of the blood pressure information included in each group by grouping the pieces of the blood pressure information according to whether measurement is performed at the workplace corresponding to the identification information G1, at the hospital corresponding to the identification information G2, before sleep corresponding to the identification information G3, during sleep corresponding to the identification information G4, after waking up corresponding to the identification information G5, and during exercise corresponding to the identification information G6. In addition, blood pressure fluctuations may occur due to workplace stress in the workplace and white-coat stress in the hospital, and blood pressure fluctuations may also occur before sleep, during sleep, after waking up, or during exercise. The blood pressure information collected in these situations can be used for health management.

For example, the situation specifying unit 1032 compares a specified number for a certain period of time (e.g. 10 days) with a number of measurements of the blood pressure information of each group during a certain period of time (e.g. 10 days), and specifies a group with a number of measurements less than the specified number as an insufficient group. Alternatively, the situation specifying unit 1032 may compare a specified number that increases in accordance with the elapsed period from the start of use of the blood pressure monitor 1 or from the first measurement date and time with a number of measurements of the blood pressure information of each group accumulated from the start of use of the blood pressure monitor 1 or from the first measurement date and time, and specify a group of numbers of measurements that is less than the specified number as an insufficient group. The specified number may be increased by one every day.

In order to prevent the occurrence of a situation in which an excessive shortage is specified, the insufficient group may be specified after the number of measurements of the blood pressure information of at least one group reaches a certain number (e.g. five). Alternatively, the insufficient group may be specified after a certain period of time (for example, one week) has elapsed from the start of use of the blood pressure monitor 1.

The situation specifying unit 1032 specifies the situation of the insufficient group as the measurement promoting situation. The measurement frequency may be calculated in place of the number of measurements of blood pressure information.

In the example of grouping in FIG. 6, for example, if the specified number is set to 10, the situation specifying unit 1032 specifies that the blood pressure information during sleep is insufficient and specifies the situation during sleep as the measurement promoting situation. The blood pressure measurement during sleep is based on a blood pressure measurement schedule. For example, the blood pressure measurement schedule includes a blood pressure measurement schedule at 2:00 a.m. As a cause of the shortage of the blood pressure information during sleep, it is considered that the blood pressure measurement function according to the blood pressure measurement schedule is turned off by the intention of the measurement subject to avoid interference with sleep.

Alternatively, in the example of grouping in FIG. 6, for example, if the specified number is set to 20, the situation specifying unit 1032 specifies that the blood pressure information during sleep and during exercise is insufficient, and specifies the situation during sleep and during exercise as the measurement promoting situation. Different specified numbers may be set for respective groups. For example, it is possible to set the specified number during sleep which is measurable during sleep every day to 10, and to set the specified number during exercise to 5 on the assumption that there is no daily exercise habit.

The situation specifying unit 1032 may compare the number of measurements of the blood pressure information among the groups during a certain period, and identify a group including only the blood pressure information of a relatively small number of measurements as an insufficient group. For example, a group including only the blood pressure information of the smallest number of measurements among the groups during a certain period may be identified as an insufficient group. It is also possible to identify, as an insufficient group, a group including only a number of measurements of the blood pressure information that does not satisfy the specified ratio with respect to the number of measurements of the blood pressure information of the group including blood pressure information having the largest number of measurements among the groups during a certain period of time. It is also possible to identify, as an insufficient group, a group including only the blood pressure information of a number measurements that is less than the average value of the number of measurements of blood pressure information included in the groups during a certain period of time. It is also possible to identify, as an insufficient group, a group including only the blood pressure information of a number of measurements that does not satisfy a specified ratio with respect to the average value of the number of measurements of blood pressure information included in the groups during a certain period of time.

The configuration of the current situation detecting unit 1033 will be described.

The current situation detecting unit 1033 detects a current situation of the measurement subject from at least one of time information, position information, acceleration information, temperature and humidity information, atmospheric pressure information, and action schedule information, and outputs the current situation to the support information output unit 1034 and the blood pressure information output unit 1036. The support information output unit 1034 determines whether or not the current situation output from the current situation detecting unit 1033 corresponds to the measurement promoting situation. The blood pressure information output unit 1036 uses the current situation output from the current situation detecting unit 1033 in accordance with the blood pressure measurement as the blood pressure measurement situation. The "detection" performed by the current situation detecting unit 1033 may be replaced with "estimation."

For example, the current situation detecting unit 1033 detects whether or not the current position corresponds to the registered position on the basis of the acquired position information (current position) and the pre-registered position information (registered position). For example, when the current position is included in a predetermined range from the registered position, it is detected that the current position corresponds to the registered position. That is, the current situation detecting unit 1033 can detect whether or not the current position corresponds to the registered position as the current situation. For example, by pre-registering at least one position of a workplace, home, a hospital, etc., it is possible to detect whether or not the current position corresponds to at least one of these positions.

The current situation detecting unit 1033 detects whether or not the current situation corresponds to various situations estimated from the acceleration information based on the acquired acceleration information. For example, the current situation detecting unit 1033 can estimate an activity amount from the acceleration information, and further detect whether or not the current situation corresponds to any of the situations of before sleep, during sleep, after waking up, etc., on the basis of the activity amount. The current situation detecting unit 1033 can detect whether or not the situation is during exercise and whether or not the situation is immediately after exercise on the basis of the activity amount information.

The current situation detecting unit 1033 detects whether or not the current situation corresponds to the situation of the action schedule information on the basis of the acquired time information (current time) and the acquired action schedule information. For example, the current situation detecting unit 1033 can detect whether the current situation corresponds to any situation such as before sleep, during sleep, or after waking up, by using the current time and the action schedule information in place of the acceleration information. For example, the current situation detecting unit 1033 detects that the current situation corresponds to during sleep on the basis of the action schedule information including the current time 23:00, the scheduled sleeping time 22:00, and the scheduled waking time 7:00.

Further, the current situation detecting unit 1033 detects a rapid temperature change based on the acquired time information and temperature and humidity information. For example, if the temperature change per predetermined time exceeds a reference value, a rapid temperature change is detected.

The configuration of the support information output unit 1034 will be described.

The support information output unit 1034 receives the measurement promoting situation from the situation specifying unit 1032, receives the current situation from the current situation detecting unit 1033, compares the current situation with the measurement promoting situation, and determines whether or not the current situation corresponds to the measurement promoting situation on the basis of the comparison result. For example, if the current situation is in the workplace and the measurement promoting situation is also in the workplace, the support information output unit 1034 determines that the current situation corresponds to the measurement promoting situation. If the current situation is during sleep and the measurement promoting situation is during sleep, the support information output unit 1034 determines that the current situation corresponds to the measurement promoting situation. If the current situation is during exercise and the measurement promoting situation is also during exercise, the support information output unit 1034 determines that the current situation corresponds to the measurement promoting situation. Note that "judgment" by the support information output unit 1034 may be replaced with "estimation."

The support information output unit 1034 outputs first support information or second support information if it is determined that the current situation corresponds to the measurement promoting situation. The first or second support information may be replaced with first or second control information. For example, the support information output unit 1034 outputs the first support information for instructing the blood pressure measuring unit 1035 to measure a blood pressure (to start blood pressure measurement). The blood pressure measuring unit 1035 measures the blood pressure on the basis of the first support information. In other words, the first support information is an instruction for the blood pressure measuring unit 1035 to measure a blood pressure.

Further, the support information output unit 1034 outputs the second support information for prompting the communication unit 108 to perform input operation (hereinafter also referred to as "input operation of blood pressure measurement") for generating an instruction for the blood pressure measuring unit 1035 to measure a blood pressure. The communication unit 108 transmits, for example, an e-mail for prompting the input operation of blood pressure measurement to a preliminarily registered destination on the basis of the second support information. For example, by preliminarily registering a destination corresponding to the mobile terminal 80, the communication unit 108 transmits, for example, an e-mail for prompting the input operation of blood pressure measurement to the mobile terminal 80. The mobile terminal 80 receives, for example, an e-mail for prompting the input operation of blood pressure measurement, and displays information for prompting the input operation of blood pressure measurement. The support information output unit 1034 outputs the second support information to the display unit 101. The display unit 101 displays information for prompting the input operation of blood pressure measurement on the basis of the second support information. For example, the second support information is information for visually prompting the input operation by characters, images, or characters and images. If the blood pressure monitor 1 has a vibration notification function, information for prompting the input operation of blood pressure measurement on the basis of the second support information may be reported by vibration of the vibration notification function. If the blood pressure monitor 1 is provided with a speaker, information for prompting the input operation of blood pressure measurement on the basis of the second support information may be reported from the speaker through voice or sound effects.

The configuration of the blood pressure measuring unit 1035 will be described.

For example, the blood pressure measuring unit 1035 measures a blood pressure value of the measurement subject by controlling various operations, as described below, on the basis of detection of the measurement instruction which is output in response to the measurement switch of the operating section 102 being pushed by the measurement subject (input operation of blood pressure measurement), or detection of a measurement instruction which triggers the start of blood pressure measurement. The measurement of the blood pressure value by the blood pressure measuring unit 1035 is to calculate the blood pressure value from the sensed data.

For example, the blood pressure measuring unit 1035 initializes a processing memory area of the storage unit 104 on the basis of the detection of the measurement instruction or the detection of the measurement instruction which triggers the start of blood pressure measurement. The blood pressure measuring unit 1035 turns off the pump 114 via the pump drive circuit 113, opens the exhaust valve built in the pump 114, and maintains the on-off valve 115 in an open state, so as to exhaust air in the pressure cuff 302 and the sensing cuff 304. The blood pressure measuring unit 1035 controls the first pressure sensor 111 and the second pressure sensor 112 to adjust their pressure of 0 mmHg. The blood pressure measuring unit 1035 turns on the pump 114 via the pump drive circuit 113, maintains the on-off valve 115 in an open state, and controls the pressure cuff 302 and the sensing cuff 304 to start application of pressure. The blood pressure measuring unit 1035 controls the pump 114 to be driven via the pump drive circuit 113 while monitoring the pressure of the pressure cuff 302 and the sensing cuff 304 by the first pressure sensor 111 and the second pressure sensor 112, respectively. The blood pressure measuring unit 1035 controls air to be sent to the pressure cuff 302 through the first channel and to the sensing cuff 304 through the second channel.

The blood pressure measuring unit 1035 waits until the pressure of the sensing cuff 304 reaches a predetermined pressure (e.g. 15 mmHg), or until the drive time of the pump 114 elapses for a predetermined time (e.g. three seconds). The blood pressure measuring unit 1035 puts the on-off valve 115 in the closed state and continues the control of supplying air from the pump 114 to the pressure cuff 302 through the first channel. As a result, pressure is gradually applied to the pressure cuff 302, and the pressure cuff 302 gradually compresses the left wrist 90. The back plate 303 transmits the compressing force from the pressure cuff 302 to the sensing cuff 304. The sensing cuff 304 compresses the left wrist 90 (including an artery-passing portion 90a).

Through this pressurization process, the blood pressure measuring unit 1035 monitors the pressure Pc of the sensing cuff 304, that is, the pressure of the arterial-passing portion 90a of the left wrist 90, by the second pressure sensor 112 in order to calculate the blood pressure value (systolic blood pressure: SBP and diastolic blood pressure: DBP, etc.), and acquires a pulse signal Pm as a fluctuation component. Based on the pulse signal Pm, the blood pressure measuring unit 1035 calculates a blood pressure value by applying a known algorithm by using an oscillometric method. After calculating the blood pressure value, the blood pressure measuring unit 1035 stops the pump 114 and, opens the on-off valve 115, so as to discharge the air in the pressure cuff 302 and the sensing cuff 304. The blood pressure measuring unit 1035 can calculate a blood pressure value by such control, and outputs the calculated blood pressure value to the blood pressure information output unit 1036 as blood pressure information.

The configuration of the blood pressure information output unit 1036 will be described.

The blood pressure information output unit 1036 receives the current situation output from the current situation detecting unit 1033 as a blood pressure measurement situation in accordance with the timing of the blood pressure measurement by the blood pressure measuring unit 1035, and outputs the blood pressure information output from the blood pressure measuring unit 1035 in association with the blood pressure measurement situation. That is, the blood pressure information output unit 1036 outputs blood pressure-related information including the blood pressure information and the blood pressure measurement situation associated with the blood pressure information to the display unit 101 and the storage unit 104. The display unit 101 displays the blood pressure-related information, and the storage unit 104 stores the blood pressure-related information. The blood pressure measuring unit 1035 repeats the blood pressure measurement, thereby storing (accumulating) a plurality of pieces of blood pressure-related information obtained by measurements made a plurality of times in the storage unit 104.

(Operation)

Figure 7:
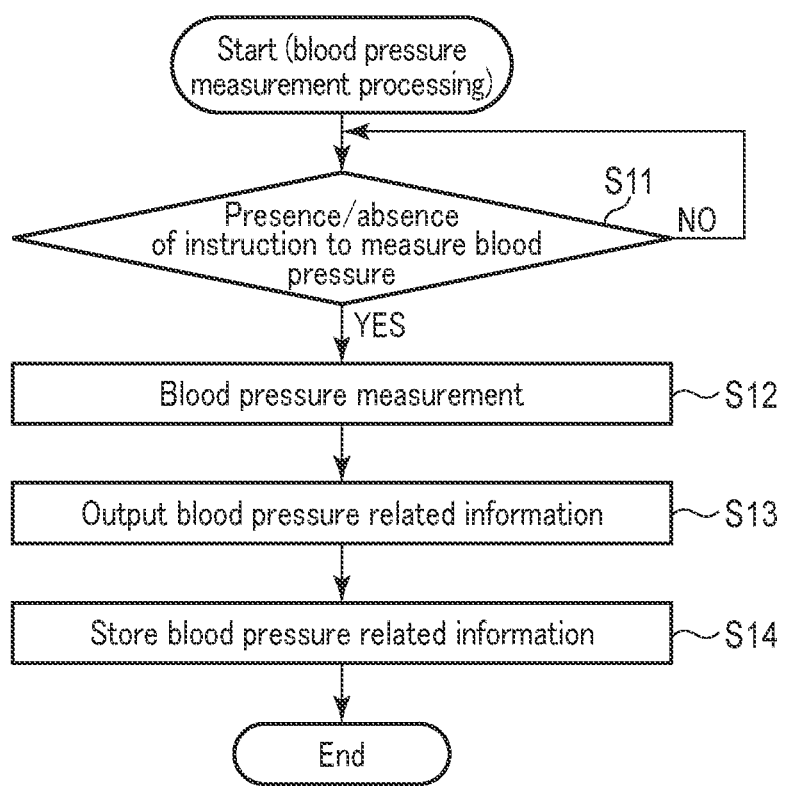
FIG. 7 is a flowchart showing an example of a blood pressure measurement processing according to an embodiment.

FIG. 7 is a flowchart showing an example of a blood pressure measurement processing according to the embodiment.

As shown in FIG. 7, for example, in a standby state in which power is supplied to the blood pressure monitor 1, the operating section 102 does not generate an instruction to measure a blood pressure unless a measurement switch is pressed by the measurement subject (input operation of blood pressure measurement) (step S11: NO), and waits for the measurement subject to press the measurement switch. The operating section 102 generates an instruction to measure the blood pressure in response to the measurement switch being pushed by the measurement subject (step S11: YES).

The blood pressure measuring unit 1035 controls the operation for blood pressure measurement on the basis of the instruction to measure the blood pressure, and measures the blood pressure information (step S12). The blood pressure measurement based on such an input instruction from the operating section 102 will be referred to as manual measurement. If a blood pressure measurement schedule is registered in the storage unit 104, the information acquisition unit 1031 acquires the blood pressure measurement schedule, and the current situation detecting unit 1033 generates an instruction to measure a blood pressure on the basis of the blood pressure measurement schedule. For example, the blood pressure measurement schedule includes information of date and time for blood pressure measurement. The current situation detecting unit 1033 generates an instruction to measure a blood pressure on the basis of the date and time for blood pressure measurement included in the blood pressure measurement schedule and the current date and time. The blood pressure measuring unit 1035 controls the operation for measuring a blood pressure on the basis of this instruction to measure a blood pressure, and measures blood pressure information. Blood pressure measurement based on such a blood pressure measurement schedule will be referred to as scheduled measurement. This embodiment includes not only manual measurement but also combined use of the manual measurement and the scheduled measurement. Factors that may cause a shortage in the number of measurements of blood pressure information according to the blood pressure measurement situation include depending on manual measurements only and combining manual measurements and scheduled measurements.

The blood pressure information output unit 1036 receives the current situation output from the current situation detecting unit 1033 as the blood pressure measurement situation, and outputs the blood pressure information output from the blood pressure measuring unit 1035 in association with the blood pressure measurement situation. In other words, the blood pressure information output unit 1036 outputs the blood pressure-related information including the blood pressure information and the blood pressure measurement situation associated with the blood pressure information to the display unit 101 and the storage unit 104 (step S13). The storage unit 104 stores blood pressure-related information. For example, by repeating blood pressure measurement, the storage unit 104 stores (accumulates) blood pressure-related information (step S14).

Figure 8:
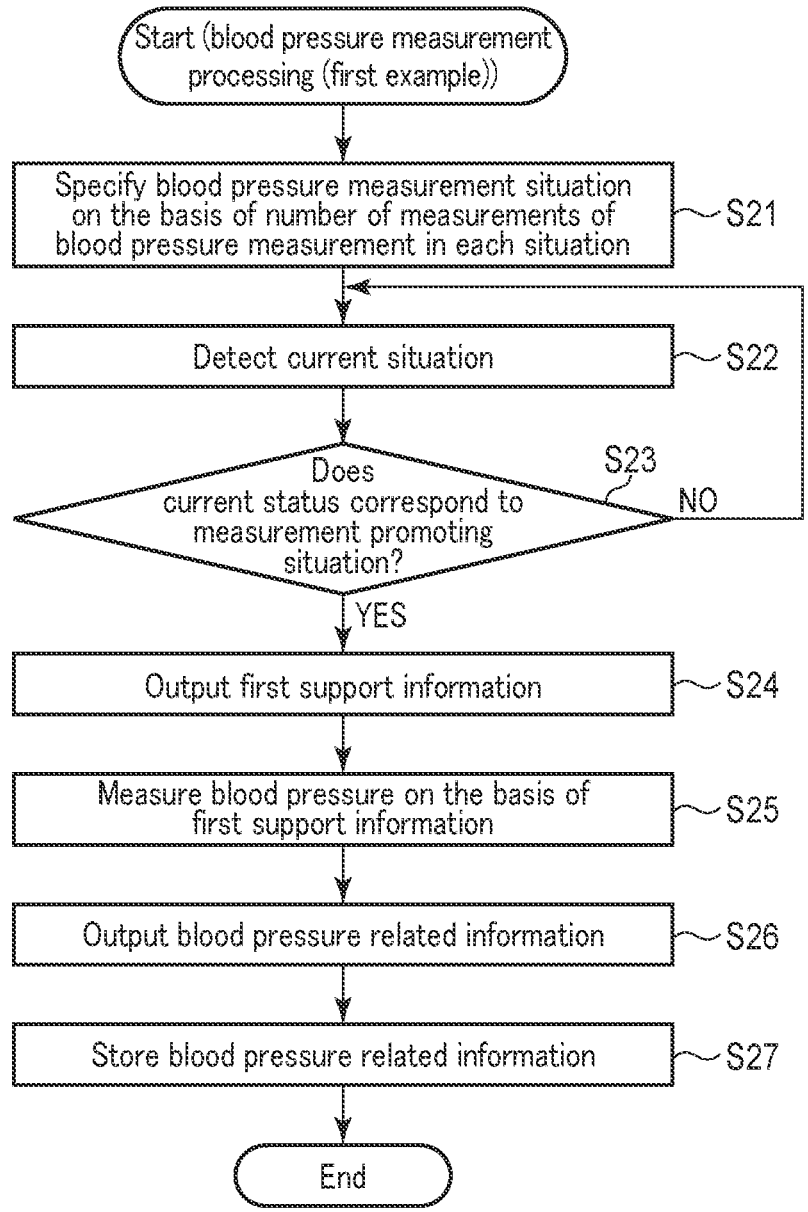
FIG. 8 is a flowchart showing a first example of the blood pressure measurement supporting process according to the embodiment.

FIG. 8 is a flowchart showing a first example of the blood pressure measurement support processing according to the embodiment.

As shown in FIG. 8, the situation specifying unit 1032 receives the blood pressure-related information from the information acquisition unit 1031, detects the number of measurements of the blood pressure information according to the blood pressure measurement situation, and identifies a part of the situation of the measurement subject to be the measurement promoting situation on the basis of the number of measurements of the blood pressure information according to the blood pressure measurement situation (step S21). For example, the situation specifying unit 1032 calculates the number of measurements of the blood pressure information included in each group on the basis of the grouping shown in FIG. 6, compares the specified number pieces of the blood pressure information during a certain period of time with the number of measurements of the blood pressure information of each group during a certain period of time, and specifies a group with a number of measurements that does not satisfy the specified number as an insufficient group. The situation specifying unit 1032 specifies the situation of the insufficient group as the measurement promoting situation. In the example of grouping in FIG. 6, for example, if the specified number is set to 20, the situation specifying unit 1032 specifies that the blood pressure information during sleep is insufficient, and specifies the situation during sleep as the measurement promoting situation.

The current situation detecting unit 1033 detects the current situation (step S22). The support information output unit 1034 receives the measurement promoting situation output from the situation specifying unit 1032, receives the current situation output from the current situation detecting unit 1033, and determines whether or not the current situation corresponds to the measurement promoting situation (step S23). For example, the support information output unit 1034 determines the current situation as the measurement promoting situation if the current situation is during sleep and the measurement promoting situation is during sleep (step S23: YES), and determines the current situation as not the measurement promoting situation if the current situation is not during sleep but the measurement promoting situation is during sleep (step ST23: NO).

If it is determined that the current situation is the measurement promoting situation, the support information output unit 1034 outputs first support information to the blood pressure measuring unit 1035 (step S24). The blood pressure measuring unit 1035 controls the operation for blood pressure measurement based on the first support information (blood pressure instrument reading), and measures blood pressure information such as the blood pressure value (step S25).

The blood pressure information output unit 1036 receives the current situation output from the current situation detecting unit 1033 as the blood pressure measurement situation, and outputs the blood pressure information output from the blood pressure measuring unit 1035 in association with the blood pressure measurement situation. That is, the blood pressure information output unit 1036 outputs, to the display unit 101 and the storage unit 104, blood pressure-related information including the blood pressure information and the blood pressure measurement situation associated with the blood pressure information (step S26). The storage unit 104 stores the blood pressure-related information (step S27).

Figure 9:
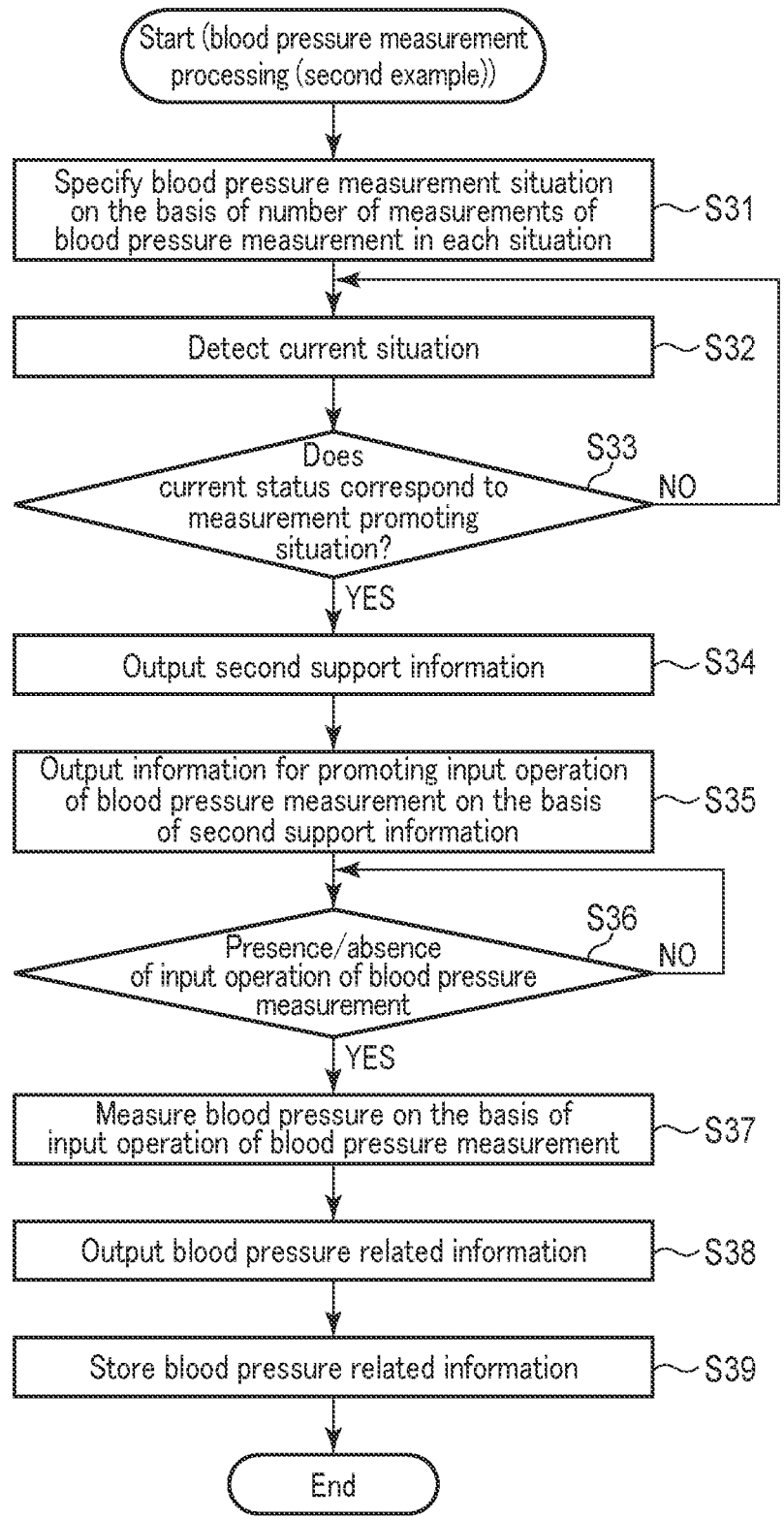
FIG. 9 is a flowchart showing a second example of the blood pressure measurement supporting process according to the embodiment.

FIG. 9 is a flowchart showing a second example of blood pressure measurement support processing according to the embodiment. Steps S31 to S33 in FIG. 9 are substantially the same as steps S21 to S23 in FIG. 8, and a description thereof is omitted.

As shown in FIG. 9, if it is determined that the current situation is the measurement promoting situation, the support information output unit 1034 outputs second support information to at least one of the display unit 101 or the communication unit 108 (step S34). The display unit 101 displays information for prompting input operation for generating an instruction for the blood pressure measuring unit 1035 to measure a blood pressure on the basis of the second support information (step S35). In addition, the communication unit 108 transmits, for example, an e-mail for prompting input operation of blood pressure measurement to a preliminarily registered destination on the basis of the second support information (step S35).

For example, the measurement subject operates (presses, etc.) the measurement switch of the operating section 102 while referring to the information for prompting the input operation of blood pressure measurement displayed on the display unit 101 (step S36: YES). Alternatively, the measurement subject operates the measurement switch of the operating section 102 upon seeing the information for prompting the input operation of blood pressure measurement in the e-mail received by the mobile terminal 80 (step S36: YES). The operating section 102 generates an instruction for the blood pressure measuring unit 1035 to measure a blood pressure in response to the operation of the measurement switch. The blood pressure measuring unit 1035 controls the operation for blood pressure measurement on the basis of the instruction to measure the blood pressure, and measures blood pressure information such as the blood pressure value (step S37).

The blood pressure information output unit 1036 receives the current situation output from the current situation detecting unit 1033 as the blood pressure measurement situation, and outputs the blood pressure information output from the blood pressure measuring unit 1035 in association with the blood pressure measurement situation. That is, the blood pressure information output unit 1036 outputs, to the display unit 101 and the storage unit 104, blood pressure-related information including the blood pressure information and the blood pressure measurement situation related to the blood pressure information (step S38). The storage unit 104 stores the blood pressure-related information (step S39).

The information output in response to the second support information may be information for prompting the registration or change of the blood pressure measurement schedule. For example, if the measurement promoting situation is during sleep, the second support information may be information for prompting, for example, the measurement subject to register the blood pressure measurement at bedtime in the blood pressure measurement schedule.

Although the case where the storage unit 104 stores the blood pressure-related information and the information acquisition unit 1031 acquires the blood pressure-related information stored in the storage unit 104 has been described, the memory of the server 70 or the mobile terminal 80 may store the blood pressure-related information in place of the storage unit 104 of the blood pressure monitor 1, and the information acquisition unit 1031 may acquire the blood pressure-related information stored in the memory of the server 70 or the mobile terminal 80.

(Advantageous Effect)

As described in detail above, in the embodiment of the present invention, a part of the situation of the measurement subject is specified as the measurement promoting situation on the basis of the number of measurements of the blood pressure information for each blood pressure measurement situation, and support information relating to blood pressure measurement is output if the current situation to be detected corresponds to the measurement promoting situation. That is, the determination that the current situation corresponds to the measurement promoting situation triggers output of the first or second support information. The output of the first or second support information supports the blood pressure measurement and recording of the measurement result in the measurement promoting situation. This makes it possible to expect an increase in the number of measurements in a situation where the number of measurements is small (for example, in a time zone where the number of measurements is small). In other words, it is expected that the insufficiency, etc. in the number of measurements of blood pressure information for each blood pressure measurement situation can be resolved.

For example, the predetermined situation is specified as measurement promoting information if blood pressure information of a predetermined situation is insufficient, first support information is output if this predetermined situation is detected, a blood pressure is measured based on the first support information, blood pressure information acquired by measurement in association with the blood pressure measurement situation (a predetermined situation) is output, and blood pressure information associated with the blood pressure measurement situation is stored. Thus, it is possible to promote the measurement and recording of the blood pressure information in the predetermined situation specified as the measurement promoting situation, and it is possible to expect a resolution of the insufficiency, etc. in the blood pressure information in the predetermined situation.

Alternatively, the predetermined situation is specified as the measurement promotion information if the blood pressure information of the predetermined situation is insufficient, the second support information is output to the measurement subject if the predetermined situation is detected, and information for promoting the input operation of blood pressure measurement is output based on the second support information. For example, information prompting input operation of blood pressure measurement is displayed. Further, an e-mail is sent to urge input operation of blood pressure measurement. If information for promoting input operation of blood pressure measurement is recognized by the measurement subject, etc., input operation of blood pressure measurement from the measurement subject, etc. can be expected. If a measurement instruction is generated in response to input operation of blood pressure measurement, blood pressure is measured based on this measurement instruction, blood pressure information acquired by measurement in association with the measurement situation (a predetermined situation) is output, and blood pressure information associated with the measurement situation is stored. This leads to promotion of the measurement and recording of the blood pressure information in the predetermined situation specified as the measurement promoting situation, and expectation of a resolution of the insufficiency, etc. in the blood pressure information in the predetermined situation.

Other Embodiments

A case has been described in which the blood pressure monitor 1 specifies the measurement promoting situation on the basis of the number of measurements of blood pressure information for each blood pressure measurement situation; however, the embodiment is not limited thereto. The measurement promoting situation may be specified in the server 70 or the mobile terminal 80, and the specified measurement promoting situation may be reported to the blood pressure monitor 1. For example, the server 70 or the mobile terminal 80 receives and stores blood pressure information associated with the blood pressure measurement situation from the blood pressure monitor 1. The server 70 or the mobile terminal 80 groups the blood pressure information associated with the blood pressure measurement situation according to the measuring situation, specifies the measurement promoting situation on the basis of the number of measurements of the blood pressure information for each blood pressure measurement situation, and notifies the blood pressure monitor 1 of the specified measurement promoting situation. If the blood pressure monitor 1 receives the measurement promoting situation from the server 70 or the mobile terminal 80 and determines that the current situation corresponds to the measurement promoting situation, the blood pressure monitor 1 outputs support information relating to blood pressure measurement. For example, the blood pressure monitor 1 may output first support information to start blood pressure measurement, or may output second support information to promote input operation of blood pressure measurement.

The case has been described in which the blood pressure monitor 1 specifies the measurement promoting situation on the basis of the number of measurements of blood pressure information for each blood pressure measurement situation, and determines whether the current situation corresponds to the measurement promoting situation; however, the embodiment is not limited thereto. If the measurement promoting situation is specified at the mobile terminal 80 and the current situation is judged to correspond to the measurement promoting situation, the blood pressure monitor 1 may be notified of information indicating that the current situation corresponds to the measurement promoting situation. For example, the mobile terminal 80 receives blood pressure information associated with the blood pressure measurement situation from the blood pressure monitor 1, and stores the blood pressure information. The mobile terminal 80 groups pieces of the blood pressure information associated with the blood pressure measurement situation according to the blood pressure measurement situation, and specifies the measurement promoting situation on the basis of the number of measurements of the blood pressure information according to the blood pressure measuring situation. Further, if the mobile terminal 80 detects the current situation and determines that the current situation corresponds to the measurement promoting situation, the mobile terminal 80 notifies the blood pressure monitor 1 of information indicating that the current situation corresponds to the measurement promoting situation. The blood pressure monitor 1 receives the notification from the mobile terminal 80 that the current situation corresponds to the measurement promoting situation, and outputs support information relating to blood pressure measurement based on this notification. For example, the blood pressure monitor 1 outputs first support information and starts blood pressure measurement.

The blood pressure monitor 1 is not limited to a type of blood pressure monitor (a non-continuous type blood pressure monitor) in which the blood pressure monitor 1 starts blood pressure measurement on the basis of input operation of blood pressure measurement by a measurement subject or a trigger signal (e.g. first support information) autonomously generated by the blood pressure monitor 1 as indicated above. For example, the blood pressure monitor 1 may be a blood pressure monitor (a continuous-type blood pressure monitor) using a pulse transmit time (PTT) method, a tonometry method, an optical method, a radio wave method, or an ultrasonic method. The PTT method is a method of measuring the pulse transmit time (PTT) and estimating a blood pressure value from the measured pulse transmit time. The tonometry method is a method in which a pressure sensor is brought into direct contact with a living body part (a measurement subject part) through which an artery such as the radial artery of the wrist passes, and the blood pressure value is measured by using information detected by the pressure sensor. The optical method, the radio wave method, and the ultrasonic method are methods in which light, radio waves, or ultrasonic waves are applied to a blood vessel and the blood pressure value is measured based on their reflected waves.

For example, assume that a continuous-type blood pressure monitor transmits blood pressure information associated with a blood pressure measurement situation to an external memory (for example, the memory of the server 70 or the mobile terminal 80), and the server 70 or the mobile terminal 80 stores the blood pressure information. Depending on a communication environment or a communication setting of the blood pressure monitor, there may be a periodical failure of transmission of blood pressure information to the server 70 or the mobile terminal 80. In such a case, the server 70 or the mobile terminal 80 may have an insufficiency in the number of measurements of the blood pressure information for each blood pressure measurement situation. Alternatively, there is a case where it is desired to suppress the amount of information accumulated in the server 70 or the mobile terminal 80, or a case where it is desired to suppress the amount of information transmitted and received between the blood pressure monitor and the server 70 or the mobile terminal 80.

In these cases, the server 70 or the mobile terminal 80 groups pieces of the blood pressure information associated with the blood pressure measurement situation according to the blood pressure measurement situation, specifies the measurement promoting situation based on the number of measurements of the blood pressure information according to the blood pressure measurement situation, and notifies the blood pressure monitor of the specified measurement promoting situation. The blood pressure monitor continuously measures a blood pressure, does not transmit all the measured blood pressure information to the server 70 or the mobile terminal 80, receives the measurement promoting situation from the server 70 or the mobile terminal 80, and transmits the measured blood pressure information to the server 70 or the mobile terminal 80 if the current situation is judged to correspond to the measurement promoting situation. This processing is expected to resolve the insufficiency, etc. in the number of measurements of blood pressure information for each blood pressure measurement situation in the server 70 or the mobile terminal 80. Furthermore, the processing enables suppression of the amount of information accumulated in the server 70 or the mobile terminal 80 and suppression of the amount of information transmitted and received.

In the first embodiment, the case where the blood pressure is measured has been described as an example. However, the embodiment is not limited thereto, and the present invention can also be applied to the measurement of other biological information such as an activity amount, a number of steps, the heart, the pulse rate, and a body temperature.

The various function units described in the above embodiments may be realized by using a circuit. The circuit may be a dedicated circuit that implements a particular function, or may be a general-purpose circuit such as a processor.

At least a part of the processing of the above embodiments can be realized by using a general-purpose computer as basic hardware. A program for realizing the above processing may be provided in such a manner that the program is stored in a computer-readable recording medium. The program is stored in the recording medium as an installable or executable file. Examples of the recording medium include a magnetic disk, an optical disk (e.g. a compact disc-read only memory (CD-ROM), compact disc-recordable (CD-R), and a digital versatile disc (DVD)), a magneto-optical disk (e.g. magneto-optical (MO)), and a semiconductor memory. The recording medium may be any medium as long as it can store a program and is computer-readable. A program for realizing the above processing may be stored on a (server) computer connected to a network such as the Internet, and may be downloaded to a (client) computer via the network.

Some or all of the above-described embodiments may be described as in the following Additional Notes, but are not limited thereto.

(Additional Note 1)

An information processing apparatus comprising: a processor configured to: specify a part of a situation of a measurement subject as a measurement promoting situation on the basis of a number of measurements of biological information for each situation of the measurement subject when the biological information of the measurement subject is measured by a biological information measuring unit;

detect a current situation of the measurement subject; and output support information relating to measurement of the biological information if the current situation corresponds to the measurement promoting situation; and a memory storing an instruction to operate the processor.

(Additional Note 2)

An information processing method implemented by the information processing apparatus configured to support operation of a biological information measuring unit, comprising:

a situation specifying process of specifying a part of a situation of a measurement subject on the basis of a number of measurements of the biological information for each situation of the measurement subject when the biological information of the measurement subject is measured by the biological information measuring unit, as a measurement promoting situation, by using at least one processor;

a current situation detecting process for detecting the current situation of the measurement subject by using the at least one processor; and an assistance information output process of outputting support information relating to measurement of the biological information when the current situation corresponds to the measurement promoting situation, by using the at least one processor.

REFERENCE SIGNS LIST

1: blood pressure monitor
10: main body
10A: case
10B: glass
10C: back cover
20: belt
30: cuff structure
30a: one end
30b: the other end
30c: inner periphery
70: server
80: mobile terminal
90: left wrist
90a: artery-passing portion
91: radial artery
92: ulnar artery
93: radius
94: ulna
95: tendon
101: display unit
102: operating section
103: control unit
104: storage unit
105: acceleration sensor
106 temperature and humidity sensor
107: atmospheric pressure sensor
108: communication unit
109: GPS receiver
110: battery
111: first pressure sensor
112: second pressure sensor
113: pump drive circuit 114: pump
115: on-off valve
201: first belt portion
201a: proximal portion
201b: distal portion
202: second belt portion
202a: proximal portion
202b: distal portion
202c: small hole
203: buckle
203A: frame-like body
203B: tongue
203C: connecting rod
204: belt holding portion
301: curler
302: pressure cuff
303: back plate
304: sensing cuff
304A: first sheet
304B: second sheet
401: connecting rod
402: connecting rod
501: flexible tube
502: flexible tube
503: first channel forming member
504: second channel forming member
1031: information acquisition unit
1032: situation specifying unit
1033: current situation detecting unit
1034: support information output unit
1035: blood pressure measuring unit
1036: blood pressure information output unit

The invention claimed is:

1. An information processing apparatus comprising:
a situation specifying unit configured to specify a part of a situation of a measurement subject as a measurement promoting situation, based on a number of measurements of biological information in each situation of the measurement subject when the biological information of the measurement subject is measured by a biological information measuring unit;
a current situation detecting unit configured to detect a current situation of the measurement subject; and
a support information output unit configured to output support information relating to measurement of the biological information if the current situation corresponds to the measurement promoting situation,
if a number of measurements of the biological information of at least one of situations of the measurement subject reaches a certain number, the situation specifying unit specifying, as the measurement promoting situation, the part of the situation of the measurement subject in which the number of the measurements of the biological information is less than a specified number.

2. The information processing apparatus according to claim 1, wherein the support information is an instruction for the biological information measuring unit to measure the biological information.

3. The information processing apparatus according to claim 1, wherein the support information is information for promoting input operation for generating an instruction for the biological information measuring unit to measure the biological information.

4. The information processing apparatus according to claim 1, wherein the situation specifying unit generates information indicating the number of the measurements of the biological information in each situation of the measurement subject, based on a situation of the measurement subject associated with each piece of biological information.

5. The information processing apparatus according to claim 1, wherein the situation specifying unit specifies, as the measurement promoting situation, the part of the situation of the measurement subject where the number of the measurements of the biological information is relatively small.

6. The information processing apparatus according to claim 1, wherein the current situation detecting unit detects at least one of time information, position information, acceleration information, temperature and humidity information, atmospheric pressure information, and action schedule information as the current situation of the measurement subject.

7. An information processing method performed by an information processing apparatus configured to support operation of a biological information measuring unit, comprising:
a situation specifying step for specifying a part of a situation of a measurement subject as a measurement promoting situation, based on a number of measurements of biological information in each situation of the measurement subject when the biological information of the measurement subject is measured by the biological information measuring unit;
a current situation detecting step for detecting a current situation of the measurement subject; and
if a number of measurements of the biological information of at least one of situations of the measurement subject reaches a certain number, the situation specifying unit specifying, as the measurement promoting situation, the part of the situation of the measurement subject in which the number of the measurements of the biological information is less than a specified number.

8. A non-transitory computer-readable storage medium storing an information processing program for causing a computer to function as each unit included in the information processing apparatus according to claim 1.

* * * * *